US007282178B2

(12) United States Patent
Salamone et al.

(10) Patent No.: US 7,282,178 B2
(45) Date of Patent: Oct. 16, 2007

(54) COMPOSITION AND METHOD FOR CLEANING LIPID DEPOSITS ON CONTACT LENSES

(75) Inventors: Joseph C. Salamone, Boca Raton, FL (US); Roya Borazjani, Fairport, NY (US); Vicki Barniak, Fairport, NY (US); Robert Manchester, Lima, NY (US); David McCanna, Pittsford, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 0 days.

(21) Appl. No.: 11/442,789

(22) Filed: May 30, 2006

(65) Prior Publication Data

US 2006/0276358 A1 Dec. 7, 2006

Related U.S. Application Data

(60) Provisional application No. 60/687,117, filed on Jun. 3, 2005.

(51) Int. Cl.

| | |
|---|---|
| ***A61L 2/18*** | (2006.01) |
| ***C11D 1/72*** | (2006.01) |
| ***C11D 3/37*** | (2006.01) |
| ***C11D 3/48*** | (2006.01) |
| ***B08B 3/04*** | (2006.01) |

(52) U.S. Cl. ........................ 422/28; 510/112; 510/421; 510/475; 510/505; 134/42

(58) Field of Classification Search ................ 510/112, 510/421, 475, 505; 422/28; 134/42

See application file for complete search history.

(56) References Cited

U.S. PATENT DOCUMENTS

| | | | | |
|---|---|---|---|---|
| 3,987,163 | A | 10/1976 | Rankin | |
| 4,436,730 | A | 3/1984 | Ellis et al. | |
| 4,820,352 | A | 4/1989 | Riedhammer et al. | |
| 4,960,799 | A | 10/1990 | Nagy | |
| 5,037,647 | A | 8/1991 | Chowhan et al. | |
| 5,209,865 | A | 5/1993 | Winterton et al. | |
| 5,401,327 | A | 3/1995 | Ellis et al. | |
| 5,447,966 | A | 9/1995 | Hermes et al. | |
| 5,604,189 | A | 2/1997 | Zhang et al. | |
| 5,773,396 | A | 6/1998 | Zhang et al. | |
| 6,037,328 | A | 3/2000 | Hu et al. | |
| 6,096,138 | A | 8/2000 | Heiler et al. | |
| 6,143,244 | A | 11/2000 | Xia et al. | |
| 6,309,658 | B1 | 10/2001 | Xia et al. | |
| 6,323,165 | B1 | 11/2001 | Heiler et al. | |
| 6,348,508 | B1 | 2/2002 | Denick, Jr. et al. | |
| 6,369,112 | B1 | 4/2002 | Xia | |
| 6,478,881 | B2 | 11/2002 | Ellis et al. | |
| 6,702,983 | B2 | 3/2004 | Hu et al. | |
| 6,790,816 | B2 | 9/2004 | Xia et al. | |
| 6,793,941 | B1 | 9/2004 | De Bruijn et al. | |
| 6,861,411 | B1 | 3/2005 | Ahmed | |
| 6,872,383 | B2 | 3/2005 | Ueno | |
| 2003/0096717 | A1 | 5/2003 | Xia et al. | |
| 2003/0109390 | A1 | 6/2003 | Salpekar et al. | |
| 2004/0119176 | A1 | 6/2004 | Xia et al. | |
| 2004/0186028 | A1* | 9/2004 | Hu et al. | 510/112 |
| 2004/0258558 | A1 | 12/2004 | Salamone et al. | |
| 2005/0118132 | A1* | 6/2005 | Xia et al. | 424/70.31 |

FOREIGN PATENT DOCUMENTS

WO WO 2004/112848 12/2004

OTHER PUBLICATIONS

Mansur et al., "Pluronic x Tetronic Polyols: Study of Their Properties and Performance in the Destabilization of Emulsions Formed in the Petroleum Industry" Science Digest, *Journal of Colloid and Interface Science*, vol. 271, Issue 1, Mar. 1, 2004, pp. 232-240.

"Pluronic® F127 Block Copolymer Surfactant," Technical Bulletin, BASF Corporation, 2002, no month given.

"Pluronic® and Tetronic® Surfactants," *Performance* Chemicsl, BASF Corporation, 1999, no month given.

"Pluronic® F123 Block Copolymer Surfactant," Technical Bulletin, BASF Corporation, 2004, no month given.

"Pluronic® 1107 Block Copolymer Surfactant," Technical Bulletin, BASF Corporation, 2002, no month given.

International Search Report (PCTISA/210) and Written Opinion (PCT/ISA/237) mailed on Sep. 27, 2006.

* cited by examiner

*Primary Examiner*—Brian Mruk

(57) ABSTRACT

This invention is directed to an aqueous composition and methods for clean lipid deposits on contact lenses. In particular, a combination of non-ionic surfactants, branched and/or straight poly(ethylene oxide-propylene oxide) (PEO-PPO) block copolymers having HLB value greater than or equal to 18, with an additional straight poly(ethylene oxide-propylene oxide) (PEO-PPO) block copolymers having HLB value less than or equal to 15, has been found to improve the lipid cleaning properties of an aqueous composition for contact lenses and prevent the overgrowth of harmful bacteria, yeast and molds without adversely affecting the comfort or safety in terms of the level of toxicity to eye tissue.

22 Claims, No Drawings

COMPOSITION AND METHOD FOR CLEANING LIPID DEPOSITS ON CONTACT LENSES

CROSS REFERENCE

This application claims the benefit of Provisional Patent Application No. 60/687,117 filed Jun. 3, 2005 and is incorporated herein by reference.

FIELD OF INVENTION

This invention relates to an aqueous composition and methods for cleaning lipid deposits and/or prevention of lipid deposition on medical devices, particularly, for contact lenses.

BACKGROUND

Contact lenses are used by an increasing number of people as means of correcting vision and/or compensating for eye abnormalities. Worldwide, about 100 million people use contact lenses. In the U.S. alone, 34 million people wear contact lenses (http://www.medicalpost.com/mpcontent/article.jsp?content=/content/EXTRACT/RAWART/3836/02B.html). However, contact lenses must usually be inserted and removed daily with scrupulous cleaning and disinfection between each wearing that requires solutions and containers.

During wear and normal handling of contact lenses, microorganisms as well as biomolecules such as lipids, proteins, etc., can adhere to the contact lenses and contaminate the storage containers/solution. Furthermore, a tear film that contains proteins, lipids, and even microorganisms covers the surface of the eye. Any of these components found in the tear film, on the external surface of the eye or the surrounding skin, can be carried into the storage containers/solution for the contact lens. Then, the microorganisms that multiplied in the storage containers/solution can transfer to the eyes via contact lenses and become a pathogen that may cause eye infection, resulting in impaired vision and blindness. Various solutions have been developed to clean these deposits and disinfect the microorganisms.

A "daily cleaner" comprised with various kinds of surfactants and disinfectants is recommended for daily use to remove most deposits and debris on contact lenses. In an approach to prevent protein deposits, contact lens solutions containing chemical agents such as cationic polymers were developed to prevent proteins from adhering to the contact lens surface of rigid gas permeable (RGP) and soft contacts lenses.

Solutions that wet the lenses before insertion in the eye are required for both the hard and soft types of contact lenses, although their formulations have tended to differ based on their different properties. After the contact lenses are inserted in the eye, ophthalmic solutions for rewetting, lubricating, and/or enhancing the comfort of the contact lens wearer are sometimes applied to the eye by means of a drop dispenser. Isotonic solutions for improving the comfort of wearing soft contact lenses by being added directly to the contact lens in the eye typically contain viscosity enhancing agents, lubricants, surfactants, buffers, preservatives, and salts.

Multipurpose solutions are popular because of the convenience of a single solution for cleaning, disinfecting and conditioning contact lenses immediately prior to insertion of the lens in the eye. Multipurpose solutions are also designed for use as a wetting agent, without rinsing, meaning that the solution must be ophthalmically safe for eye contact. This limits, to some extent, the type and concentration of both cleaning agents and biocides that can be employed in the solution as a preservative or disinfectant tends to be irritating to the eye. Additionally, the surface active agents must not inhibit the wetting or conditioning function of the solution.

U.S. Pat. No. 4,820,352 (Riedhammer et al.) discloses compositions for cleaning and conditioning contact lenses, where the primary cleaning agent is a specific class of polyethyleneoxy-polypropyleneoxy block copolymer adduct of ethylene diamine (also known as poloxamine). This patent describes compositions which are sufficiently nonirritating that a contact lens treated with the solution can be inserted directly in the eye.

U.S. Pat. No. 5,209,865 (Winterton et al.) discloses a conditioning solution for contact lenses that comprises a combination of a poloxamine and a poloxamer surfactant each having an HLB (hydrophilic-lipophilic balance) of seven or below. This patent describes a solution forming a uniform hydrophilic film on a lens surface for which proteins have very little affinity for a prophylactic effect to the lens.

U.S. Pat. No. 5,604,189 and U.S. Pat. No. 5,773,396 (Zhang et al.) disclose a composition for cleaning and wetting contact lenses comprising (i) a non-amine polyethyleneoxy-containing compound having an HLB of at least about 18, (ii) a surface active agent having cleaning activity for contact lens deposits that may have an HLB less than 18, and (iii) a wetting agent. An ethoxylated glucose derivative such as glucam can be employed as the wetting agent, also disclosed in U.S. Pat. No. 5,401,327 to Ellis et al. In another approach, Tyloxapol is employed as a conventional surface active agent in a multipurpose solution, which agent has cleaning activity for contact-lens deposits and has an HLB less than 18.

There has been a constant need for ophthalmic solutions with better lipid cleaning properties. The deposits from cellular debris, protein, and lipid accumulated over time can adsorb to the surface of contact lenses and irritate the eyes. Particularly, lipid deposits can reduce the transparency and impair the performance of the contact lenses. Lipid deposits on RGP or silicone hydrogel lenses during wear generate a hydrophobic surface that is not easily rewetted with currently used types and concentrations of surfactants in the lens care compositions.

There is, therefore, a need for a composition with improved lipid cleaning properties while maintaining or increasing the biocidal efficacy of the product without adversely affecting comfort or safety in terms of the level of toxicity to eye tissue. It would also be desirable to have a composition that can be utilized as an eye drop, an eyewash solution, a contact lens care solution or a cleaning solution, a storing solution, a disinfectant, a cleaning-storing solution, and a cleaning disinfecting-storing solution. The invention answers these needs.

SUMMARY OF INVENTION

The invention is directed to an aqueous composition for cleaning lipid deposits and/or prevention of lipid deposition on a medical device, particularly a contact lens. An aqueous composition according to the invention comprises (a) a branched chain polyether surfactant having an HLB value greater than or equal to 18 and (b) a straight chain polyether surfactant having an HLB value less than or equal to 15. The surfactant (b) is present in an amount effective to improve the lipid cleaning effect of the composition. In one aspect of the invention, the aqueous composition may further comprise (c) a straight chain polyether surfactant having an HLB value greater than or equal to 18. According to the invention, the combined amount of surfactants (a), (b) and (c) of the composition may preferably range from about 2.5 to about 7.0 weight percent and more preferably from 3.0 to 6.0 weight percent.

The invention also provides methods of cleaning lipids and/or prevention of lipid deposition on a medical device with the aqueous composition of the invention. According to a preferred embodiment, the composition is sufficiently nonirritating that the aqueous composition can be administered directly in the eye for use as eye drops or as a lens care solution. In another preferred embodiment, contact lenses, prior to placement in the eye, are soaked in an aqueous composition of multipurpose solution for cleaning lipid deposits.

The objects, features, and advantages of the various embodiments of the present invention will become more readily apparent from the following detailed description.

DETAILED DESCRIPTION OF THE INVENTION

This invention is directed to aqueous compositions for cleaning lipid deposits and/or prevention of lipid deposition on medical device, especially on contact lenses, and methods of using these compositions. The term "cleaning lipid deposits" includes preventing, removing, and/or reducing the formation of lipid deposits. Combinations according to the invention have been found to improve the lipid cleaning properties for contact lenses and prevent the overgrowth of harmful bacteria and molds without adversely affecting the comfort or safety in terms of the level of toxicity to eye tissue.

It has also been found that a combination of branched and straight chain polyether surfactants is not only effective in cleaning lipid deposits, but is comfortable for use in the eye. The aqueous composition of the invention is believed to reduce the hydrophobicity of the lens surface, especially in the case of a silicone hydrogel, which may reduce the affinity of lipids to the lens surface. The combination of branched and straight chain polyether surfactants according to the invention may not only prevent the deposition of lipids, but also to some extent may loosen deposits on the lens, wherein removal is assisted by the natural cleaning action of blinking.

A branched chain polyether surfactant is considered to be a star-type polymer, such as a tetra-polyether substituted derivative of ethylenediamine, or the like. A linear polyether surfactant is considered to have no branched or graft junctions, but may include pendant functional groups.

Ophthalmic lenses can generally be subdivided into two major classes, namely hydrogel and rigid gas permeable lenses. Hydrogel lenses are either the traditional type, such as these derived from 2-hydroxyethyl methacryl or of silicone hydrogels, such as those derived from siloxanyl monomers and macromonomers. Rigid permeable lenses do not absorb appreciable amounts of water, whereas hydrogels can absorb and retain water in an equilibrium state. Hydrogels are widely used as soft contact lens materials. It is known that increasing the hydrophilicity of the contact lens surface improves the wettability of the contact lenses. This in turn is associated with improved wear comfort of contact lenses. Additionally, the surface of the lens can affect the overall susceptibility of the lens to deposition of proteins and lipids from the tear fluid during lens wear. Accumulated deposits can cause eye discomfort or even inflammation.

The aqueous compositions of the invention can be used with all types of contact lenses such as conventional hard, soft and rigid gas permeable lenses as well as silicone hydrogels. The term "soft lens" is meant a lens having a proportion of hydrophilic repeat units such that the water content of the lens during use is at least 20% by weight. The term "soft contact lens" as used herein generally refers to those contact lenses that readily flex under small amounts of force. Typically, soft contact lenses are formulated from polymers having a certain proportion of repeat units derived from 2-hydroxyethyl methacrylate and/or other hydrophilic monomers or macromonomers, typically crosslinked with a crosslinking agent. However, newer soft lenses, especially for extended wear, are being made from high-Dk siloxane-containing materials.

The aqueous compositions according to the invention for cleaning lipid deposits and/or prevention of lipid deposition on a medical device advantageously contain beneficial compositions of surfactants which yield highly effective lipid cleaning. Various other surfactants suitable for use in the invention are disclosed in McCutcheon's Detergents and Emulsifiers, North American Edition, McCutcheon Division, MC Publishing Co., Glen Rock, N.J. 07452 and the CTFA International Cosmetic Ingredient Handbook, Published by The Cosmetic, Toiletry, and Fragrance Association, Washington, D.C.

According to the invention, an aqueous composition for cleaning lipid deposits and/or prevention of lipid deposition on a medical device comprising:

(a) a branched chain polyether surfactant having an HLB value greater than or equal to 18; and (b) a straight chain polyether surfactant having an HLB value less than or equal to 15, wherein the surfactant (b) is present in an amount effective to improve the lipid cleaning effect of the composition.

The aqueous composition of the invention may further comprising:

(c) a straight chain polyether surfactant having an HLB value greater than or equal to 18.

According to the invention, the combined amount of surfactants (a), (b) and (c) is from about 2.5 to about 7.0 weight percent.

The branched chain polyether surfactants (a) in the aqueous compositions of the invention comprise one or more chains or polymeric components having oxyalkylene (—O—R—) repeats units wherein R has 2 to 6 carbon atoms. Representative polyether surfactants comprise block polymers of two or more different kinds of oxyalkylene repeat units, the ratio of which determining the HLB of the surfactant. The branched chain polyether surfactants employed in the invention can be selected, for example, from the group of commercially available surfactants having the name poloxamine or poloxamer, as adopted by The CTFA International Cosmetic Ingredient Dictionary. Such surfactants are available from BASF Wyandotte Corp., Wyandotte, Mich., under the registered trademark "Tetronic™ (BASF)."

The straight chain polyether surfactants (b) or (c) in the aqueous compositions of the invention also comprise one or more chains or polymeric components having oxyalkylene (—O—R—) repeats units wherein R has 2 to 6 carbon atoms as described above. The straight chain polyether surfactants are available from BASF Wyandotte Corp., Wyandotte, Mich., under the registered trademark "Pluronic™ (BASF)." For convenience purposes, the branched chain and straight chain surfactants employed in the aqueous composition disclosed herein will be referred to as Tetronic and Pluronic respectively, and with a numerical suffix to identify a particular grade of material.

Tetronic and Pluronic are block copolymers consisting of propylene oxide (PO) and ethylene oxide (EO) blocks—specifically, they are poly(a-oxyethylene-b-oxypropylene-a-oxyethylene) triblock copolymers. Their solubility in water is generally good, but the properties of the individual block copolymers vary substantially. The nomenclature used for the block copolymers, and generally herein, is such that the first two figures, when multiplied by 100, represent the average molecular weight of the PO block, whilst the last figure, when multiplied by 10, represents the ethylene oxide content (% w/w) of the poloxamer. Thus, for Pluronic F127, the average molecular weight of the PO block is 12000 Daltons with 70% w/w/ethylene oxide content.

Grades of Tetronic and Pluronic surfactants available with molecular weights ranging from as low as 1650 to 27,000. Properties of each grade within the series vary depending on the percent of hydrophilic units poly(oxyethylene) and molecular weight of hydrophobic units poly(oxypropylene) in the adduct. While all members within the series exhibit wetting and detergency properties, it was discovered that only certain members are suitable for use in the cleaning and conditioning solutions disclosed herein, due to the wide variation in performance characteristics regulated by their hydrophilic-hydrophobic balance. The Tetronic and Pluronic surfactants found suitable are those capable of demonstrating maximum cleaning efficiency in dispersing both protein and lipid deposits at ambient and elevated temperatures at lowest solution concentration without trade-offs in lens compatibility and toxicity levels, i.e. maintaining the lowest potential as an irritant to eye tissues.

To illustrate, Tetronic surfactants, having molecular weights of less than 7500 and having hydrophilic chains of about 10 weight percent poly(oxyethylene) units, have the most effective detergent properties, but are substantially immiscible in aqueous solutions at 25° C. Consequently, Tetronic Series 701™ through Tetronic 1501™ would be unsuitable for use in the aqueous contact lens cleaning solutions described herein. Similarly, solutions having only 20 weight percent hydrophilic units like Tetronic 702™™, Tetronic 1102™, Tetronic 1302™ and Tetronic 1502™ although miscible in aqueous medium and possessing superior detergency properties, they nevertheless were found to have too high a potential for irritating eye tissues. The aqueous composition of the invention preferably employs the solid grades of Tetronic surfactant, particularly those having from about 60 to about 80 percent by weight poly (oxyethylene) hydrophilic units.

Suitable branched and straight chain polyether surfactants having an HLB value greater than or equal to 18, (a) and (c) of the aqueous composition of the invention, include for example but are not limited to Pluronic $F_{38}$™ (BASF) having a HLB of 31 and average molecular weight (AMW) of 4700; Pluronic F68™ (BASF) having a HLB of 29 and AMW of 8400; Pluronic 68LF™ (BASF) having a HLB of 26 and AMW or 7700; Pluronic F77™ (BASF) having a HLB of 25 and AMW of 6600; Pluronic $F_{87}$™ (BASF) having a HLB of 24 and AMW of 7700; Pluronic F88™ (BASF) having a HLB of 28 and AMW or 11400; Pluronic F98™ (BASF) having a HLB of 28 and AMW of 13000; Pluronic F108™ (BASF) having a HLB of 27 and AMW of 14600; Pluronic F127™ (BASF) having a HLB of 22 and AMW of 12600; Pluronic L35™ (BASF) having a HLB of 19 and AMW of 1900; Tetronic 707™ (BASF) having a HLB of 27 and AMW of 12200; Tetronic 908™ (BASF) having a HLB of 31 and AMW of 25000; Tetronic 909™ (BASF) having a HLB of 32 and AMW of 30000; Tetronic 1107™ (BASF) having a HLB of 24 and AMW of 15000; Tetronic 1307™ (BASF) having a HLB of 24 and AMW of 18000; and Tetronic 1508™ (BASF) having a HLB of 27 and AMW of 30000.

The preferred branched chain poly(ethylene oxide-propylene oxide-ethylene oxide) (PEO-PPO-PEO) block copolymers having an HLB value greater than or equal to 18, Tetronic surfactants, employed in the invention are Tetronic 707™, Tetronic 908™, Tetronic 909™, Tetronic 1107™, Tetronic 1307™, and Tetronic 1508™. Most preferred Tetronic surfactants are Tetronic 707™, 1107™ and 1307™. The preferred straight chain poly(ethylene oxide-propylene oxide-ethylene oxide) (PEO-PPO-PEO) block copolymers having HLB value greater than or equal to 18, Pluronic surfactants, are Pluronic F38™, Pluronic F68™, Pluronic 68LF™, Pluronic F77™, Pluronic F87™, Pluronic F88™, Pluronic F98™, Pluronic F108™, and Pluronic F127™. Most preferred Pluronic surfactants are Pluronic F127™.

Suitable straight chain polyether surfactants having an HLB value less than or equal to 15, (c) of the aqueous compositions of the invention, include for example but are not limited to Pluronic P123™ (BASF) having a HLB of 8 and average molecular weight (AMW) of 5750 and Pluronic P105™ (BASF) having a HLB of 15 and AMW of 6500.

The HLB of a surfactant is known to be a major factor in determining the emulsification characteristics of a polyether surfactant. In general, surfactants with lower HLB values are more lipophilic, while surfactants with higher HLB values are more hydrophilic. The HLB values of various poloxamines and poloxamers are provided by BASF Wyandotte Corp., Wyandotte, Mich.

Relatively high HLB values greater than about 18, or even more preferably 22 or higher, indicate a lower affinity for both hydrophobic molecules and/or surfaces, such as lipids and hydrophilic molecules. According to the invention, a combination of the branched chain poly(ethylene oxide-propylene oxide-ethylene oxide) (PEO-PPO-PEO) block copolymers having HLB value of greater than or equal to 18, Tetronic, with the straight chain poly(ethylene oxide-propylene oxide-ethylene oxide) (PEO-PPO-PEO) block copolymers having an HLB value of 15 or below, Pluronic, demonstrates an unexpected, enhanced cleaning lipid properties for contact lenses. The straight poly(ethylene oxide-propylene oxide-ethylene oxide) (PEO-PPO-PEO) block copolymers having an HLB value of 15 or below, Pluronic, is present in an amount effective to improve the lipid cleaning effect of the composition. Preferably, the straight poly(ethylene oxide-propylene oxide-ethylene oxide) (PEO-PPO-PEO) block copolymers having an HLB value of 15 or below, Pluronic, is present from about 0.01 weight percent to 2 weight percent, and most preferably, from 0.05 weight percent to 1.5 weight percent.

Additional straight chain poly(ethylene oxide-propylene oxide-ethylene oxide) (PEO-PPO-PEO) block copolymers having an HLB value of greater than or equal to 18 may be added to the aqueous composition of the invention. The combined amount of branched chain and straight chain polyether surfactants in the aqueous composition is from about 2.5 to about 7.0 weight percent. The branched and the straight chain polyether surfactants having an HLB values greater than 18, (a) and (c) of the aqueous composition, used in combination in about a 1:2 ratio have been found to significantly decrease lipid affinity to the surface of contact lenses and are effective in removing lipids from the surface of contact lenses without mechanical or digital cleaning.

Such polyether surfactants, the branched and the straight chain polyether surfactants, (a) and (c) of the aqueous compositions, are employed in the invention in total combined amounts ranging from about 0.1 to about 8.0 weight percent, preferably from about 2.5 to about 7.0 weight percent to achieve cleaning efficacy. More preferably, the total combined amounts range from 3.0 to 6.0 weight percent.

The aqueous composition according to the invention are physiologically compatible. Specifically, the solution must be "ophthalmically safe" for use with a contact lens, meaning that a contact lens treated with the solution is generally suitable and safe for direct placement on the eye, that is, the solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO (International Standards Organization) standards and U.S. FDA (Food & Drug Administration) regulations. The solution should be sterile in that the absence of microbial contaminants in the product prior to release must be statistically demonstrated to the degree necessary for such products.

An aqueous composition of the invention can be applied in the form of an eye drop, or a contact lens care solution. The eye drop solution can be selected from the group consisting of a solution to soothe eye irritation, a moisturizing solution, a contact lens rewetting solution, and a contact lens lubricating solution. The contact lens care solution can be selected from the group consisting of a cleaning solution, a storing solution, a disinfecting solution, a conditioning solution, a wetting solution and a multipurpose solution.

According to various preferred embodiments of the invention, the compositions are likewise suitable for disinfecting a contact lens soaked therein. In addition to water, it is preferred that the compositions also include at least one antimicrobial agent, especially a non-oxidative antimicrobial agent that derives its antimicrobial activity through a chemical or physicochemical interaction with organisms. So that the contact lenses treated with the composition may be instilled directly in the eye, i.e., without rinsing the contact lens with a separate composition, the antimicrobial agent needs to be an ophthalmically acceptable antimicrobial agent.

Suitable antimicrobial agents for use in the invention include quaternary ammonium salts. Suitable quaternary ammonium salts for use in the invention include for example but are not limited to poly[(dimethyliminio)-2-butene-1,4-diyl chloride] and [4-tris(2-hydroxyethyl)ammonio]-2-butenyl-co-[tris(2-hydroxyethyl)ammonio]dichloride (Chemical Abstracts Registry Number 75345-27-6) generally available as Polyquaternium-1® from Onyx Corporation. Also suitable are biguanides and their salts, such as 1,1'-hexamethylene-bis[5-(2-ethylhexyl)biguanide] (Alexidine) and poly (hexamethylene biguanide) (PHMB), available from ICI Americas, Inc., Wilmington Del. under the trade name Cosmocil CQ, benzalkonium chloride (BAK) and sorbic acid.

One or more antimicrobial agents are present in the compositions in an amount effective for disinfecting a contact lens, as found in conventional lens soaking and disinfecting solutions. Preferably, the antimicrobial agent will be used in a disinfecting amount or an amount from about 0.0001 to about 0.5 weight percent by volume. A disinfecting amount of an antimicrobial agent is an amount that will at least partially reduce the microorganism population in the formulations employed. Typically, such agents are present in concentrations ranging from about 0.00001 to about 0.5 weight percent based on volume (w/v), and more preferably, from about 0.00003 to about 0.05 weight percent.

Contact lens care solutions require disinfection and or preservative compliance with FDA (510 (k)) Guidance Document for contact lens products. These procedures measure the extent of viability loss of representative microorganisms at established time intervals to determine the extend of viability loss. FDA (510 (k)) Guidance Document's recommended test organisms for both disinfecting standalone and preservative efficacy testing are composed of three bacteria (*Pseudomonas aeruginosa* ATCC 9027, *Stapylococcus aureus* ATCC 6538, and *Serratia marcescens* ATCC 13880) and two fungi (*Candida albicans* ATCC 10231, and *Fusarium solani* ATCC 36031). The performance requirement biocidal stand alone testing calls for 3 log reduction for bacterial cells and 1 log reduction for each fungi. At day 28, after the rechallenge on day 14, the performance requirement for preservative efficacy testing calls for reduction of 3.0 logs per bacteria and ±0.5 for fungi.

Aqueous compositions of the invention may also contain various other components including for example but not limited to one or more chelating and/or sequestering agents, one or more osmolality adjusting agents, one or more surfactants, one or more buffering agents and/or one or more wetting agents. Chelating agents, also referred to as sequestering agents, are frequently employed in conjunction with an antimicrobial agent. These agents bind heavy metal ions, which might otherwise react with the lens and/or protein deposits and collect on the lens. Chelating agents are well known in the art, and examples of preferred chelating agents include ethylenediaminetetraacetic acid (EDTA) and its salts, especially disodium EDTA. Such agents are normally employed in amounts from about 0.01 to about 2.0 weight percent, more preferably from about 0.01 to about 0.3 weight percent. Other suitable sequestering agents include gluconic acid, citric acid, tartaric acid and their salts, e.g., sodium salts.

Aqueous compositions of the invention may be designed for a variety of osmolalities, but it is preferred that the compositions range from hypotonic to isotonic with respect to eye fluids. Specifically, it is preferred that the compositions have an osmotic value of less than about 350 mOsm/kg, more preferably from about 175 to about 330 mOsm/kg, and most preferably from about 240 to about 310 mOsm/Kg. One or more osmolality adjusting agents may be employed in the composition to obtain the desired final osmolality. Examples of suitable osmolality adjusting agents include, but are not limited to sodium and potassium chloride, monosaccharides such as dextrose, calcium and magnesium chloride, and low molecular weight polyols such as glycerin and propylene glycol. Typically, these agents are used individually in amounts ranging from about 0.01 to 5 weight percent and preferably, from about 0.1 to about 2 weight percent.

Aqueous compositions of the invention have an ophthalmically compatible pH, which generally will range between about 6 to about 8, and more preferably between 6.5 to 7.8, and most preferably about 7 to 7.5. One or more conventional buffers may be employed to obtain the desired pH value. Suitable buffers include for example but are not limited to borate buffers based on boric acid and/or sodium borate, phosphate buffers based on $Na_2HPO_4$, $NaH_2PO_4$ and/or $KH_2PO_4$, citrate buffers based on sodium or potassium citrate and/or citric acid, sodium bicarbonate, aminoalcohol buffers, Good buffers and combinations thereof. Generally, buffers will be used in amounts ranging from about 0.05 to about 2.5 weight percent, and preferably, from about 0.1 to about 1.5 weight percent.

Aqueous compositions may likewise include a wetting agent, to facilitate the composition wetting the surface of a contact lens. Within the art, the term "humectant" is also commonly used to describe these materials. A first class of wetting agents are polymer wetting agents. Examples of suitable wetting agents include for example but are not limited to poly(vinyl alcohol) (PVA), poly(N-vinylpyrrolidone) (PVP), cellulose derivatives, guar derivatives, and poly(ethylene glycol). Cellulose derivatives and PVA may be used to also increase viscosity of the composition, and offer this advantage if desired. Specific cellulose derivatives include for example but are not limited to hydroxypropylmethylcellulose, hydroxypropylcellulose, carboxymethylcellulose, methylcellulose, hydroxyethylcellulose, and cationic cellulose derivatives. As disclosed in U.S. Pat. No. 6,274,133, cationic cellulosic polymers also help prevent accumulation of lipids and proteins on a hydrophilic lens surface. Such cationic cellulosic polymers include for example but are not limited to water soluble polymers commercially available under the CTFA (Cosmetic, Toiletry, and Fragrance Association) designation Polyquaternium-10, including the cationic cellulosic polymers available under the trade name UCARE® Polymers from Amerchol Corp., Edison, N.J., such as for example but not limited to Polymer JR™. Generally, these cationic cellulose polymers contain quaternized N,N-dimethylamino groups along the cellulosic polymer chain.

Another suitable class of wetting agents is non-polymeric wetting agents. Examples may include glycerin, propylene glycol, and other non-polymeric diols and glycols. The specific quantities of wetting agents used in the invention will vary depending upon the application. However, the wetting agents will typically be included in an amount from about 0.01 to about 5 weight percent, preferably from about 0.1 to about 2 weight percent.

It will be understood that some constituents possess more than one functional attribute. For example, cellulose derivatives are suitable polymeric wetting agents, but are also referred to as "viscosity increasing agents" to increase viscosity of the composition if desired. Glycerin is a suitable non-polymeric wetting agent but is also may contribute to adjusting tonicity.

Aqueous compositions of the invention can be utilized as an eye drop solution or contact lens care solution by optimizing the concentration of the disinfectant or preservative agent in case of an eye-drop formula or biocidal agent for multipurpose solution. When used as an eye drop solution, the aqueous composition may soothe eye irritation, act as a moisturizer, as a contact lens rewetting solution, or as a contact lens lubricating solution. The contact lens care solution is selected from the group consisting of a cleaning solution, a storing solution, a disinfecting solution, a conditioning solution, a wetting solution, or a multi-purpose solution. Preferably, aqueous compositions are applied in the form of drops to a contact lens while it is worn in the eye and which is useful for rewetting or lubricating the lens as well as for prophylactically cleaning the lens by preventing the deposition of lipids.

Such aqueous compositions can be used to prevent the overgrowth of harmful Gram positive and Gram-negative bacteria such as *Pseudomonas aeruginosa, Serratia marcescens* and *Staphyllococcus aureus,* as well as harmful molds and yeast on the lens surfaces during wear, or during the soak time, while being gentle and non-toxic against corneal epithelial cells.

The invention is especially useful for cleaning a contact lens while it is worn in the eye. Thus, as mentioned above, aqueous compositions according to the invention are especially advantageous with people who are prone to heavy lipid or like deposition or who wear lenses under an extended wear, or continuous wear regime. Extended wear is defined as a lens that is worn overnight, during sleep, preferably capable of wear for a week or more. Continuous wear is defined as a lens that is worn for at least a month.

The aqueous compositions of the invention are typically sold in a wide range of small volume containers from 1 to 30 ml in size, preferably 1 ml to 20 ml in size. Such containers can be made from HDPE (high density polyethylene), LDPE (low density polyethylene), polypropylene, poly(ethylene terepthalate) and the like. Flexible bottles having conventional drop dispensing tops are especially suitable for use with the present invention. Solutions according to the invention may suitably be applied as follows. During wear, about one or two drops are placed directly onto each lens whenever needed. Thereafter, the wearer should blink several times. It is also possible to use a spray mist to deliver the formulation to the eye.

The aqueous composition of the invention may be effectively used in both cleaning lipid deposits and/or prevention of lipid deposition on both hard and soft type contact lenses during wear while the lenses are in the eye. Additionally, the prevention and/or cleaning of the lipid deposits can be achieved by any of the well-recognized Rub and Rinse, or No Rub regimen methods recommended by the manufacturers prior to soaking the lenses in a lens case for a recommended soaking time ranging from 4 to 12 hours.

In addition to the soaking method, the solutions disclosed herein are adaptable for use in other type of equipment such as ultrasonic cleaners. Furthermore, because the solutions are also stable when heated to temperatures in the range of 80° to 90° C. They are also adaptable for use with high temperature disinfecting methods. Typically, lenses are heated to 80° C. in a disinfecting unit containing the cleaning and conditioning solution for a time period of at least 10 minutes, removed and rinsed with isotonic saline.

The following specific experiments and examples demonstrate the compositions and methods of the present invention. However, it is to be understood that these examples are for illustrative purposes only and do not purport to be wholly definitive as to conditions and scope. All percentages are by weight of the solution, unless indicated otherwise.

EXAMPLES

In the examples below, certain chemical ingredients are identified by the following abbreviations.

HAP: HAP buffer, phosphate-buffered saline (PBS) with 0.5 U of aprotinin per ml-0.05% human serum albumin-3 mM D-glucose Polymer JR®: cationic polysaccharide, polyquaternium-10

Alexidine 2HCl: quaternary ammonium salt. 1,1'-hexamethylene-bis[5-(2-ethylhexyl)biguanide]

Example 1

Table 1 lists the ingredients of the aqueous composition of the invention. Basic formulation prepared in accordance with the formulation set forth below in Table 1 was used in the aqueous compositions of Table 2, Table 3, and Table 4 with various combinations of Tetronic and Pluronic copolymers.

TABLE 1

| Basic Formulation | |
|---|---|
| Ingredient | % w/w |
| Sodium Chloride | 0.047-0.19 |
| Boric Acid | 0.85 |
| Sodium Phosphate (Monobasic) | 0.15 |
| Sodium Phosphate (Dibasic) | 0.31 |
| HAP | 0.1 |
| Polymer JR | 0.02 |
| Various combination of Pluronic and Tetronic Copolymers set forth in Table 2, Table 3, and Table 4 | 3.5-5 |
| Alexidine 2HCl | 3.0 |

pH = 6.9-7.1
Osmo. (mOsmo/Kg) = 220-300

Table 2a shows the results of the effect of preservative efficacy of an aqueous composition providing superior lipid cleaning capabilities and toxicity data. The results indicate that the addition of the straight chain polyether surfactant, Pluronic, with the branched chain polyether surfactant, Tetronic, enhanced the lipid cleaning value of the aqueous composition. Toxicity data was generated using a cell culture model for predicting the ocular irritation potential of new contact lens care compositions (Na-Fluorescent permeability assay). All these formulations have shown permeability values below the level of control. The control is a currently marketed and safe ophthalmic care product.

TABLE 2a

| Surfactants | HLB | | | | | |
|---|---|---|---|---|---|---|
| Pluronic F127 | 22 | | 3% | 3% | | |
| Pluronic P105 | 15 | | | 0.1% | | 0.1% |
| Tetronic 1107 | 24 | | 1.5% | 1.5% | 4.5% | 4.5% |
| Pluronic P123 | 8 | | 0.1% | | | |
| Formulation # | | | 18 | 21 | 49 | 51 |
| Lipid Cleaning Value | | | 456 | 390 | 42 | 84 |
| Toxicity (Fluorescent Unit) | | | 177 | 35 | 143 | 139 |
| *S. aureus* | | 14 day | Passed | Passed | Passed | Passed |
| | | 28 day | Passed | Passed | Passed | Passed |
| *P. aeruginosa* | | 14 day | Passed | Passed | Passed | Passed |
| | | 28 day | Passed | Passed | Passed | Passed |
| *E. Coli* | | 14 day | Passed | Passed | Passed | Passed |
| | | 28 day | Passed | Passed | Passed | Passed |
| *C. albicans* | | 14 day | Passed | Passed | Passed | Passed |
| | | 28 day | Passed | Passed | Passed | Passed |
| *A. niger* | | 14 day | Passed | Passed | Passed | Passed |
| | | 28 day | Passed | Passed | Passed | Passed |

Tabel 2b shows the results of biocidal stand-alone testing of an aqueous composition providing superior lipid cleaning capabilities and toxicity data. All disinfection tests are completed according to SOP 24-T008-02 (ISO Stand Alone Procedure for Disinfecting Products). The solutions were evaluated based on the performance requirement referred to as the "Stand-Alone Procedure for Disinfecting Products" (hereafter the "stand-alone test") and is based on the Disinfection Efficacy Testing for contact lens care products under the Premarket Notification (510(k)) Guidance Document For Contact Lens Care Products dated May 1, 1997, prepared by the U.S. Food and Drug Administration, Division of Ophthalmic Devices. This performance requirement does not contain a rub procedure. This performance requirement is comparable to current ISO standards for disinfection of contact lenses (revised 1995). The stand-alone test challenges a disinfecting product with a standard inoculum of a representative range of microorganisms and establishes the extent of viability loss at pre-determined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per mL must be reduced by a mean value of not less than 1.0 log within the minimum recommended disinfection time with no increase at four times the minimum recommended disinfection time. The criteria for the regimen testing is the recovery of less than 10 cfu per contact lens per challenge microorganism (Table 2c).

TABLE 2b

| Surfactants | HLB | Soak Time | | | | |
|---|---|---|---|---|---|---|
| Pluronic F127 | 22 | | 3% | 3% | 2.5% | 2.5% |
| Pluronic P105 | 15 | | | 0.1% | 0.1% | |
| Tetronic 1107 | 24 | | 1.5% | 1.5% | 1.25% | 1.25% |
| Pluronic P123 | 8 | | 0.1% | | | 0.1% |
| Alexidine(ppm) | | | 5.5 | 5.5 | 4.5 | 4.5 |
| Formulation # | | | 71 | 72 | 67 | 68 |
| Lipid Cleaning Value | | | | | | |
| Toxicity (Fluorescent Unit) | | | | | | |
| Study # 04-BCZ | | | 399-S | 399-S | 399-S | 399-S |
| *S. aureus* | | 1 hour | 2.6 | 2.9 | 2.3 | 2.5 |
| | | 4 hour | 3.3 | 3.9 | 3.5 | 3.5 |
| *P. aeruginosa* | | 1 hour | >4.9* | >4.9 | 3.9 | >4.9 |
| | | 4 hour | >4.9 | >4.9 | >4.9 | >4.9 |
| *S. macescens* | | 1 hour | 3.5 | 3.9 | 4.1 | 3.1 |
| | | 4 hour | >4.8 | >4.8 | 4.2 | >4.8 |
| *C. albicans* | | 1 hour | 2.6 | 2.8 | 3.4 | 3.1 |
| | | 4 hour | 3.3 | 4.2 | 3.9 | 4.1 |
| *F. solani* | | 1 hour | 4.5 | 4.3 | 3.8 | 4.2 |
| | | 4 hour | >4.5 | >4.5 | >4.5 | >4.5 |

*>Indicates 100% kill

TABLE 2c

| No Rub with a Rinse for the Regimen data for RGP lens for Solutions 67, 68, 79, 87 | | |
|---|---|---|
| Challenge Organism | Lens Type Average CFU Recovered | Meets Acceptance Criteria |
| *S. aureus* ATCC 6538 | <1 | Yes |
| *C. albicans* ATCC10231 | <1 | Yes |

Lipid cleaning studies were done based on a spectrophotometric measurement of the suspension, which includes the mixture of an orange dye (Sudan I) with cholesterol. Ten ml volume of formulations was tested for their ability of dissolving the lipid for 24 hour in room temperature. The higher the absorbance values, the higher the lipid cleaning efficacy of the formulations. Addition of 0.1% of P105 (High HLB value of 15) as well as P123 (HLB of 8) have statistically increased the lipid cleaning values from their control compositions.

Table 3, Table 4 and Table 5 show various combinations of branched and/or straight chain poly(ethylene oxide-propylene oxide-ethylene oxide) (PEO-PPO-PEO) block copolymers having HLB values greater than or equal to 18 with an additional straight poly(ethylene oxide-propylene oxide-ethylene oxide) (PEO-PPO-PEO) block copolymer having HLB value less than or equal to 15 which has been found to improve the lipid cleaning properties of an ophthalmic composition for contact lenses and prevent the overgrowth of harmful bacteria, yeast and molds without adversely affecting the comfort or safety in terms of the level of toxicity to eye tissue.

TABLE 3

| Surfactants | HLB | | | |
|---|---|---|---|---|
| Pluronic F127 | 22 | 3% | 3% | 3% |
| Pluronic P105 | 15 | | | |
| Tetronic 1107 | 24 | 1.5% | 1.5% | 1.5% |
| Pluronic P123 | 8 | 0.1% | 0.05% | 0.01% |
| Formulation # | | 18 | 19 | 20 |
| Lipid Cleaning Value | | 582 | 562 | 527 |

TABLE 4

| Surfactants | HLB | | | |
|---|---|---|---|---|
| Pluronic F127 | 22 | 3% | 3% | 3% |
| Pluronic P105 | 15 | 0.1% | 0.05% | 0.01% |
| Tetronic 1107 | 24 | 1.5% | 1.5% | 1.5% |
| Pluronic P123 | 8 | | | |
| Formulation # | | 21 | 22 | 23 |
| Lipid Cleaning Value | | 575 | 547 | 527 |

TABLE 5

| Surfactants | HLB | | | |
|---|---|---|---|---|
| Pluronic F127 | 22 | 3% | 2.5% | 2.5% |
| Pluronic P105 | 15 | 0.1% | 0.25% | |
| Tetronic 1107 | 24 | 1.5% | 1.25% | 1.25% |
| Pluronic P123 | 8 | | | 0.25% |
| Formulation # | | 62 | 74 | 73A |
| Lipid Cleaning Value | | 581 | 591 | 610 |

The invention claimed is:

1. An aqueous composition for cleaning lipid deposits or for minimizing lipid deposition on a contact lens, said composition comprising:

a poloxamine having an HLB value greater than or equal to 18;

a poloxamer having an HLB value less than or equal to 15, and is present in an amount effective to improve the lipid cleaning effect of the composition;

a straight chain polyether surfactant having an HLB value greater than or equal to 18;

one or more antimicrobial agents present in an amount effective to disinfect or preserve the composition; and a buffering agent, and an osmolality adjusting agent, wherein the osmolality adjusting agent is present to provide an osmolality of from 200 to 400 mOsm/kg.

2. The aqueous composition of claim 1, wherein the weight ratio of the poloxamine to the straight chain polyether surfactant having an HLB value greater than or equal to 18 is about one to two.

3. The aqueous composition of claim 1, wherein the poloxamine is selected from the group consisting of poloxamine 707, poloxamine 908, poloxamine 1107, poloxamine 1307 and poloxamine 1508.

4. The aqueous composition of claim 1 wherein the straight chain polyether surfactant having an HLB value greater than or equal to 18 is selected from the group consisting of poloxamer 105, poloxamer 108, poloxamer 188, poloxamer 217, poloxamer 237, poloxamer 238, poloxamer 288, poloxamer 338 and poloxamer 407.

5. The aqueous composition of claim 1, wherein the poloxamer having an HLB value less than or equal to 15 are poloxamer 403 and poloxamer 335.

6. The aqueous composition of claim 1, wherein the poloxamer having an HLB value less than or equal to 15 is present from about 0.01 weight percent to 2 weight percent.

7. The aqueous composition of claim 1, wherein the buffer agent is selected from the group consisting of borate buffers, citrate buffers, aminoalcohol buffers, Good buffers, phosphate buffers, and mixtures thereof to maintain a pH from about 6 to about 8.

8. A method of cleaning lipid deposits or minimizing lipid deposition on a contact lens in the eye, the method comprising administering aqueous eye drop to the eye, the composition comprising:

(a) a poloxamine having an HLB value greater than or equal to 18; and (b) a poloxamer having an HLB value less than or equal to 15, and is present in an amount effective to improve the lipid cleaning effect of the composition;

a straight chain polyether surfactant having an HLB value greater than or equal to 18;

one or more antimicrobial agents present in an amount effective to preserve the composition; and a buffering agent, and an osmolality adjusting agent, wherein the osmolality adjusting agent is present to provide an osmolality of from 200 to 400 mOsm/kg.

9. The method of claim 8, wherein the weight ratio of the poloxamine to the straight chain polyether surfactant having an HLB value greater than or equal to 18 is about one to two.

10. A method of cleaning lipids and/or prevent lipid deposition on a contact lens while worn on an eye comprising:

(i) soaking prior to placement on an eye contact lens in an aqueous composition comprising:

(a) a poloxamine having an HLB value greater than or equal to 18;

a straight chain polyether surfactant having an HLB value greater than or equal to 18; and a poloxamer having an HLB value less than or equal to 15, and is present in an amount effective to improve the lipid cleaning effect of the composition, and (ii) directly placing the treated contact lens in an eye of the wearer.

11. The method of claim 10, wherein the weight ratio of of the poloxamine to the straight chain polyether surfactant having an HLB value greater than or equal to 18 is about one to two.

12. The aqueous composition of claim 1, wherein the one or more antimicrobial agents is selected from the group consisting of 4-tris(2-hydroxyethyl) ammonio]-2-butenyl-ω-[tris(2-hydroxyethyl)ammonio]dichloride, poly(hexamethylene biguanide) and alexidine.

13. The method of claim 8, wherein the one or more antimicrobial agents is selected from the group consisting of 4-tris(2-hydroxyethyl)ammonio]-2-butenyl-ω-[tris(2-hydroxyethyl)ammonio]dichloride, poly(hexamethylene biguanide) and alexidine.

14. The aqueous composition of claim 1, further comprising a wetting agent selected from the group consisting of poly(vinylpyrrolidone), hydroxypropylmethyl cellulose and propylene glycol.

15. The method of claim 8, wherein the composition further comprises a wetting agent selected from the group consisting of poly(vinylpyrrolidone), hydroxypropylmethyl cellulose and propylene glycol.

16. The aqueous composition of claim 1, wherein the poloxamer having an HLB value less than or equal to 15 is present from 0.01 wt. % to 0.25 wt. %.

17. The method of claim 8, wherein the poloxamer having an HLB value less than or equal to 15 is present from 0.01 wt. % to 0.25 wt. %.

18. The method of claim 10, wherein the poloxamer having an HLB value less than or equal to 15 is present from 0.01 wt. % to 0.25 wt. %.

19. The method of claim 8, wherein the poloxamer having an HLB value less than or equal to 15 is present from about 0.01 wt. %to 2 wt. %.

20. The method of claim 10, wherein the poloxamer having an HLB value less than or equal to 15 is present from about 0.01 wt. %to 2 wt. %.

21. The method of claim 10, wherein the composition further comprises one or more antimicrobial agents selected from the group consisting of 4-tris(2-hydroxyethyl)ammonio]-2-butenyl-ω-[tris(2-hydroxyethyl)ammonio]dichioride, poly(hexamethylene biguanide) and alexidine.

22. The method of claim 10, further comprising a wetting agent selected from the group consisting of poly(vinylpyrrolidone), hydroxypropylmethyl cellulose and propylene glycol.

* * * * *